US006951726B2

(12) United States Patent
Bilodeau et al.

(10) Patent No.: US 6,951,726 B2
(45) Date of Patent: Oct. 4, 2005

(54) **REAL-TIME PCR ASSAY OF THE BACTERIUM *EDWARDSIELLA ICTALURI* IN CHANNEL CATFISH**

(75) Inventors: Anita L. Bilodeau, Cleveland, MS (US); William R. Wolters, Cleveland, MS (US); Geoffrey C. Waldbieser, Cleveland, MS (US); David J. Wise, Leland, MS (US)

(73) Assignees: Mississippi State University, Mississippi State, MS (US); The United States of America as represented by the Department of Agriculture, Washington, DC (US)

( * ) Notice: Subject to any disclaimer, the term of this patent is extended or adjusted under 35 U.S.C. 154(b) by 297 days.

(21) Appl. No.: 10/252,357

(22) Filed: Sep. 24, 2002

(65) Prior Publication Data

US 2004/0058332 A1 Mar. 25, 2004

(51) Int. Cl.⁷ ............................ C12Q 1/68; C12P 19/34; C07H 21/02; C07H 21/04
(52) U.S. Cl. ........................ 435/6; 435/91.2; 536/23.1; 536/24.3; 536/24.32; 536/24.33
(58) Field of Search .................... 435/6, 91.2; 536/23.1, 536/24.3, 24.32, 24.33

(56) References Cited

U.S. PATENT DOCUMENTS

| 6,316,195 B1 | 11/2001 | Frederick et al. |
| 6,355,435 B1 | 3/2002 | Wilson et al. |
| 6,387,652 B1 | 5/2002 | Haugland et al. |

OTHER PUBLICATIONS

Baldwin, T.J., et al., "Pathogenesis of Enteric Septicemia of Channel Catfish, Caused by *Edwardsiella ictaluri*: Bacteriologic and Light and Electron Microscopic Findings", Journal of Aquatic Animal Health, 5, 189–198 (1993).
Bell, K.S., et al., "Detection and Quantification of *Spongospora subterranea* f. sp. *Subterranea* in Soils and on Tubers Using Specific PCR Primers", European Journal of Plant Pathology, 105, 905–915 (1999).
Francis–Floyd, R., et al., "Effect of Water Temperature on the Clinical Outcome of Infection with *Edwardsiella ictaluri* Channel Catfish", JAVMA, 191, 11, 1413–1416 (1987).
Hawke, J.P., et al., "*Edwardsiella ictaluri* sp. nov., the Causative Agent of Enteric Septicemia of Catfish", Int'l. Journal of Systematic Bacteriology, 31, 4, 396–400 (1981).
Kimura, B., et al., "Rapid, Quantitative PCR Monitoring of Growth of *Clostridium botulinum* Type E in Modified–Atmosphere–Packaged Fish", Applied and Environmental Microbiology, 67, 1, 206–216 (2001).
Klesius, P., "Transmission of *Edwardsiella ictaluri* from Infected, Dead to Noninfected Channel Catfish", Journal of Aquatic Animal Health, 6, 180–182 (1994).
Klesius, P., et al., "Development and Evaluation of an Enzyme–Linked Immunosorbent Assay for Catfish Serum Antibody to *Edwardsiella ictaluri*", Journal of Aquatic Animal Health, 3, 94–99 (1991).

Leal–Klevezas, D.S., et al., "Single–Step PCR for Detection of *Brucella* spp. from Blood and Milk of Infected Animals", Journal of Clinical Microbiology, 33, 12, 3087–3090 (1995).
León, G., et al., "A PCR–Based Assay for the Identification of the Fish Pathogen *Renibacterium salmoninarum*", FEMS Microbiology Letters, 115, 131–136 (1994).
Makino, S–I, et al., "Direct Detection of *Bacillus anthracis* DNA in Animals by Polymerase Chain Reaction", Journal of Clinical Microbiology, 31, 3, 547–551 (1993).
Miriam, A., et al., "PCR and Probe–PCR Assays To Monitor Broodstock Atlantic Salmon (*Salmo solar* L.) Ovarian Fluid and Kidney Tissue for Presence of DNA of the Fish Pathogen *Renibacterium salmoninarum*", Journal of Clinical Microbiology, 35, 6, 1322–1326 (1997).
Newton, J.C., et al., "Pathology of Experimental Enteric Septicaemia in Channel Catfish, *Ictalurus punctatus* (Rafinesque), Following Immersion–Exposure to *Edwardsiella ictaluri*", Journal of Fish Diseases, 12, 335–347 (1989).
Nogva, H.K., et al., "Application of the 5'–Nuclease PCR Assay in Evaluation and Development of Methods for Quantitative Detection of *Campylobacter jejuni*", Applied and Environmental Microbiology, 66, 9, 4029–4036 (2000).
Nogva, H.K., et al., "Detection and Quantification of *Salmonella* in Pure Cultures Using 5'–Nuclease Polymerase Chain Reaction", International Journal of Food Microbiology, 51, 191–196 (1999).
Plumb, J.A., et al., "Survival of *Edwardsiella ictaluri* in Pond Water and Bottom Mud", The Progressive Fish–Culturist, 48, 212–214 (1986).
Rogers, W.A., "Serological Detection of Two Species of *Edwardsiella* Infecting Catfish", Int'l Symposium on Fish Biologies: Serodiagnostics and Vaccines, 49, 169–172 (1981).
Shoemaker, C.A., et al., "Protective Immunity Against Enteric Septicaemia in Channel Catfish, *Ictalurus punctatus* (Rafinesque), Following Controlled Exposure to *Edwardsiella ictaluri*", Journal of Fish Diseases, 20, 361–368 (1997).
Shotts, E.B., et al., "Pathogenesis of Experimental *Edwardsiella ictaluri* Infections in Channel Catfish (*Ictalurus punctatus*)", Can. J. Fish Aquat. Sci., 43, 36–42 (1986).
Vishnubhatla, A., et al., "Rapid 5' Nuclease (TaqMan) Assay for Detection of Virulent Strains of *Yersinia enterocolitica*", Applied and Environmental Microbiology, 66, 9, 4131–4135 (2000).
Wise, D.J., et al., "Effect of Feeding Frequency and Romet–Medicated Feed on Survival, Antibody Response, and Weight Gain of Fingerling Channel Catfish *Ictalurus punctatus* After Natural Exposure to *Edwardsiella ictaluri*", Journal of the World Aquaculture Society, 29, 2, (1998).

*Primary Examiner*—Jeffrey Fredman
*Assistant Examiner*—Teresa Strzelecka
(74) *Attorney, Agent, or Firm*—DLA Piper Rudnick Gray Cary US LLP

(57) ABSTRACT

A rapid and sensitive PCR-based assay is provided to facilitate early detection of *Edwardsiella ictaluri* in channel catfish. This bacteria is the causative agent in the disease, Enteric septicemia of catfish (ESC). Also provided is a method of selecting breeding stock for use in selective breeding programs to improve disease resistance in channel catfish. Also provided is a method of determining the efficacy of vaccines produced against ESC.

9 Claims, 3 Drawing Sheets

REAL-TIME PCR ASSAY OF THE BACTERIUM *EDWARDSIELLA ICTALURI* IN CHANNEL CATFISH

This invention was made with Government support under Grant No. 58-6402-7-022 awarded by the U.S. Department of Agriculture, Agriculture Research Service. The Government may have certain rights in this invention.

FIELD OF THE INVENTION

The invention relates to a novel genetically based highly specific detection assay for a bacterium responsible for causing disease in catfish. More particularly, the invention provides a real-time PCR assay which is specific for the detection of the pathogenic bacterium *Edwardsiella ictaluri* in blood and tissue samples of the channel catfish, *Ictalurus punctatus*.

BACKGROUND OF THE INVENTION

Conventional methods for the detection of disease in the commercial fish production industry is limited to bacterial cell culture and biochemical testing following natural outbreaks of disease. This slow and reactive process is inadequate to protect this valuable industry from the economic losses that can result from infectious diseases of fish.

While efforts have been made in the development of real-time PCR assays for the detection of particular pathogens in plants and humans, none have been developed to assist in disease prevention and control in commercial catfish farms. The present invention involves the development of a real-time PCR assay for detection of the leading pathogen affecting commercial catfish farms in the southeastern United States.

Enteric septicemia of catfish (ESC) is among the most prevalent and costly disease affecting channel catfish (*Ictalurus punctatus*) commercial production. The causative agent of ESC is the gram-negative bacterium *Edwardsiella ictaluri* (Hawke, et al., 1981). Pathogen uptake occurs primarily through the gut, nares, and gills (Baldwin and Newton, 1993) and appears to be facilitated by active feeding during periods of disease outbreak (Wise and Johnson, 1998). Progression of ESC is usually rapid, most significantly affecting fingerlings (Francis-Floyd, et al., 1987), with clinical disease signs manifesting within a few days post-infection followed by death usually within one to two weeks (Wise, et al., 1997). Resistant fish may harbor the pathogenic bacteria in macrophages, however it is unclear what role the engulfed bacteria play in later outbreaks of infection (Shoemaker and Klesius, 1997). *Edwardsiella ictaluri* is known to persist in pond sediments for at least one month (Plumb and Quinlan, 1986). While the pathology of the disease is well documented (Shotts, et al., 1986; Newton, et al., 1989; Baldwin and Newton, 1993), a better understanding of the rate of pathogen clearance would improve efforts in selective breeding for disease resistance and assist management of disease outbreaks in farm populations by providing methods of evaluating transmission rates occurring in natural outbreaks.

Currently, bacterial cell culture and biochemical testing are the primary means of detecting *Edwardsiella ictaluri* in natural outbreaks. Tissue samples are cultured for 48 hours on blood-heart infusion agar (BHI) followed by biochemical analysis to confirm putative bacterial infection. By this time, fish are typically exhibiting external signs of infection and the spread and progression of the disease throughout the population is likely (Klesius, 1994). Sensitivity of culturing assays is relatively poor, resulting in reliable detection of the bacterium only at moderate to high concentrations. Other more rapid methods (FAT and ELISA) have been developed for ESC detection (Rogers, 1981; Klesius, et al., 1991), but also lack reliability at low levels of infection (Nogva and Lillehaug, 1999; Nogva, et al., 2000).

Detection assays using PCR-based technologies have been developed for a variety of pathogens that occur in fish, soil, and other systems (Makino, et al., 1993; Leon, et al., 1994; Leal-Klevezas, et al., 1995; Mariam, et al., 1997; Nogva and Lillehaug, 1999; Bell, et al., 1999; Nogva, et al., 2000; Vishnubhatla, et al., 2000; Kimura, et al., 2001). These assays typically provide greater levels of sensitivity than traditional diagnostic tools (bacterial cell culture and characterization, immunological, and serological assays). Until recently, accurate quantitative assessment of pathogen levels has been problematic when infection levels are low.

A need therefore exists for an early, fast, effective method of detecting the causative agent, *Edwardsiella ictaluri*, of Enteric Septicemia of catfish (ESC).

SUMMARY OF THE INVENTION

The method of the present invention can be used to provide a diagnostic method for detecting disease in fish. More particularly, the method of the present invention provides a real-time detection assay for the bacterium *Edwardsiella ictaluri*.

The present invention also provides a method of selecting breeding stock for use in selective breeding programs for the purpose of improving disease resistance in fish. More particularly, the present invention provides a method of selecting disease resistant breeding stock for use in breeding programs to produce channel catfish having improved disease resistance against infection by *Edwardsiella ictaluri*.

The present invention can provide a method of measuring the efficacy of vaccines that are developed to prevent infection of fish by *Edwardsiella ictaluri*.

The present invention thus can be used by diagnostic laboratories and management agencies to predict early onset of bacterial infection in fish. Early detection may enable appropriate treatment regimes which will reduce the chance of catastrophic infection in large commercial fish populations. The invention may also be applied to research to improve the efficacy of a vaccine developed for ESC.

DETAILED DESCRIPTION OF THE INVENTION

Enteric septicemia of catfish (ESC) is the most prevalent disease affecting commercial catfish farms. The causative agent of ESC is the pathogenic bacterium *Edwardsiella*

*ictaluri*. The ESC detection assays that are currently in practice do not have the capability of detecting low levels of *Edwardsiella ictaluri* either in the blood or in water samples, while treatment of the ponds is still a viable option.

Real-time polymerase chain reaction (PCR) is an existing research technique that utilizes specifically engineered DNA sequences (two primers and a fluorescently labeled probe) to detect and quantify target sequences of DNA. The probe contains a fluorescent reporter dye on one end and a quencher dye on the other. During each amplification cycle, the probe (SEQ ID NO.:3) first attaches to the target sequence of DNA, followed by attachment of the primers (SEQ ID NO.:1 and SEQ ID NO.:2). As the DNA strand is copied, the reporter dye is released from the probe and emits a fluorescent signal. The amount of fluorescence increases with each cycle of PCR in proportion to the amount of target DNA. This results in direct detection and quantification of the target DNA sequence with a high degree of specificity (no false positives), accuracy, and sensitivity.

Figure 1:
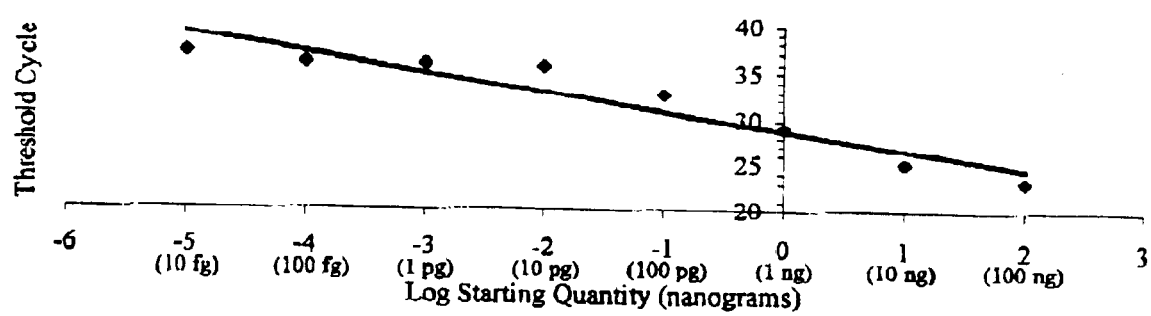
FIG. 1 depicts the standard curve for real-time PCR amplification of *Edwardsiella ictaluri* target sequence. Log values correspond to 10 fg, 100 fg, 1 pg, 10 pg, 100 pg, 1 ng, 10 ng, and 100 ng of bacterial DNA. Threshold cycle refers to the cycle at which fluorescence was first measured. $R^2=0.9582$, $Y=2.0402x+28.805$.

A set of DNA primers and a DNA probe that are specific for *Edwardsiella ictaluri* were developed for molecular detection and quantification of *Edwardsiella ictaluri* with real-time PCR technology (Table 1). Specificity of the primers and probe were assessed with 10 species of bacteria that are either biochemically similar and/or are potential contaminants in pond fish samples. Table 2 provides the classifications of the 10 species of bacteria, which did not demonstrate amplification with *Edwardsiella ictaluri*—specific primers. Each of the listed species are biochemically similar to *Edwardsiella ictaluri* and represent potential contaminants in natural ponds. Sensitivity of the assay was determined to be as low as 2 cell equivalents of bacterial DNA. The assay was validated by comparison of real-time PCR quantitation results and standard bacterial plate counts from whole blood taken from 9 fish that were experimentally infected with ESC (FIG. 1).

The invention can be used to identify fish that have active infections of ESC and surviving fish that may be harboring bacteria in their tissues. This ability to readily identify fish infected by or carrying the bacteria can be of significant benefit to both selective breeding and disease management programs. The real-time PCR assay of the present invention can be used to track disease progression and identify specific families of catfish that demonstrate innate resistance to *Edwardsiella ictaluri* infection. This information can lead to improved disease resistance through selective breeding programs. In terms of disease management, early diagnosis of ESC is extremely important for successful treatment because disease progression can be rapid and devastating to commercial farm ponds. Currently, there are no ESC diagnostic tests that facilitate early detection and quantification within both the time frame and level of sensitivity of the real-time PCR assay of the present invention. A means of sensitive and accurate early detection and quantification of ESC is needed for selective breeding and disease monitoring programs in the catfish industry. The present invention satisfies that need.

The development of real-time PCR has provided a reliable assay for quantification. This technology is based on a dual-labeled probe that anneals to the target sequence prior to the primers. As the primers anneal and are extended along the target sequence, the 5' nuclease activity of the DNA polymerase cleaves the fluorescent dye attached to the probe (the reporter dye), causing it to fluoresce. The amount of fluorescence is proportional to the amount of amplified PCR product. This technology confers higher specificity (due to the requirement that not only 2 primers, but also a probe must anneal properly to the template strand in order for amplification to occur), more accurate, and typically more sensitive than conventional PCR.

Sensitive detection of ESC is important to the successful development of a selective breeding program focused on ESC resistance. Therefore, a real-time PCR assay was developed for early detection of ESC in channel catfish blood. Specifically, three validation tests of the assay were performed 1) specificity of the target sequence as compared to other species of bacteria, 2) the level of sensitivity of detection of pure *Edwardsiella ictaluri* culture and in mixtures of bacterial DNA with genomic DNA from uninfected catfish blood, and 3) detection and quantification of the pathogen in blood samples of experimentally challenged fish.

EXAMPLES

Bacterial Strain and Culturing Information

A frozen culture of *Edwardsiella ictaluri* (S97-773) was streaked onto BHI agar plates and allowed to incubate for 48 hours at 27° C. An isolate colony was aseptically removed

TABLE 1

Primers and dual-labeled probe for specific detection of *Edwardsiella ictaluri*.

| Primers/probe | Sequence (5'-3') | Denaturation temp (° C.)* |
|---|---|---|
| Primers | | |
| Forward (SEQ ID NO.:1) | ACTTATCGCCCTCGCAACTC | 66.2 |
| Reverse (SEQ ID NO.:2) | TGATCTTCTGCTGTGGGCTG | 65.4 |
| Probe   (SEQ ID NO.:3) | CCTCACATATTGCTTCAGCGTCGAC | |

*calculated in GeneRunner version 3.04 (Hastings Software, Inc.)

TABLE 2

| Species |
|---|
| *Flavobacter columnaris* |
| *Aeromonas hydrophila* |
| *Edwarsiella tarda* |
| *Escherichia coli* |
| *Acinetobacter twoffii* |
| *Enterobacter cloacae* |
| *Klebsiella pneumoniae* |
| *Pseudomonas aeruginosa* |
| *Serratia adoifera* |
| *Proteus vulgaris* | from the agar and used to inoculate a 10 ml BHI broth culture. The culture was allowed to incubate for 24 hours at 27° C., at which time a sample from the culture was removed and enumerated using standard plate count methods on tryptic soy agar plates supplemented with 5% sheep's blood. Additionally, 10 species of biochemically similar bacteria (*Flavobacter columnaris, Aeromonas hydrophila, Edwarsiella tarda, Escherichia coli, Acinetobacter twoffli, Enterobacter cloacae, Klebsiella pneumoniae, Pseudomonas aeruginosa, Serratia adoifera, Proteus vulgaris*) were cultured in 10 ml of BHI broth as above. These 10 species were subsequently used for tests of specificity of the primer/probe set. Each species is considered to be a potential contaminant in natural ponds.

Sample Collection

Approximately 150 $\mu$l of blood was drawn from the caudal vasculature of 9 healthy fingerling channel catfish (*I punctatus*—strain NWAC 103 from USDA-ARS Catfish Genetics Research Unit, Stoneville, Miss.) into Vacutainer® tubes (Becton Dickinson Vacutainer Systems, Franklin Lakes, N.J., U.S.A.) containing 68 $\mu$l of 7.5% $K_3$ EDTA. The mean fish weight was 20 g. The collected blood samples were stored at $-80°$ C.

The same 9 fingerling channel catfish were anesthetized in 60 mg/L of tricaine methansulfonate, injected IP with 0.2 mL of the above *Edwardsiella ictaluri* culture and placed in 80-L aquaria containing 24 L of well water (flow rate=0.95 L/minute). Each fish was then removed from the aquaria 24 hours post infection and blood was collected as above. The number of *Edwardsiella ictaluri* cells/mL of blood sample was enumerated using standard plate count methods. This data was compared with real-time PCR detection levels to determine the accuracy of the detection assay.

DNA Isolation

Protocol 1: DNA Isolation From Whole Blood

The DNA isolation from whole blood protocol was modified from Leal-Klevezas, et al. (1995). For each fish, a 100 $\mu$l sub-aliquot of whole blood was centrifuged at 4000×g for 3 minutes. The supernatant was removed and 250 $\mu$l of Erythrocyte Lysis Solution (155 mM $NH_4Cl$, 10 mM $NaHCO_3$, 100 mM EDTA) was added. After centrifugation at 4000×g for 3 minutes, the supernatant was removed and this process was repeated until the pellet of cells was colorless. To each sample, 200 $\mu$l of Lysis Buffer (10 mM Tris-HCl pH 8.0, 0.5 mM EDTA, 400 mM NaCl, 1% SDS) containing 10 $\mu$g proteinase-K was added, followed by incubation at 50° C. for 30 minutes. After incubation, 400 $\mu$l of saturated buffered phenol (pH 8.0) was added and each sample was mixed thoroughly and centrifuged at 8000×g for 5 minutes. The aqueous layer was transferred to a fresh microfuge tube and an equal volume of chloroform:isoamyl alcohol (24:1) was added. After centrifugation at 8000×g for 5 minutes, the upper layer was transferred to a fresh tube and 200 $\mu$l of 7.5 M $NH_4OAc$ was added. Samples were placed on ice for 10 minutes and then centrifuged at 8000×g for 5 minutes. The aqueous layer was transferred to a fresh tube and mixed with two volumes of 95% ethanol. These samples were placed at $-80°$ C. for 30 minutes, centrifuged at 8000×g for 5 minutes, the supernatant was discarded, and the pellet was washed in 1 mL of 70% ethanol. The pellets were lyophilized to remove any traces of ethanol, resuspended in 15 $\mu$l of Millipore-filtered deionized $H_2O$ and stored at $-20°$ C. until used in PCR amplification.

Protocol 2: DNA Isolation From Bacterial Cell Cultures

One ml of culture was centrifuged at 14,000×g for 2 minutes and the supernatant was discarded. The pellet was resuspended in 600 $\mu$l Lysis buffer (10 mM Tris 7.5, 100 mM EDTA, 1% SDS) and incubated at 80° C. for 5 minutes. For each tube, 200 $\mu$l of 7.5 M $NH_4OAc$ was then added and the sample was vortexed briefly, centrifuged at 14,000×g for 4 minutes, and the supernatant was transferred to a new microfuge tube containing 600 $\mu$l isopropanol. After gentle inversion, the sample was centrifuged at 14,000×g for 1 minute to pellet the DNA. Each pellet was washed with 70% ETOH, lyophilized, and resuspended in 25 $\mu$l of filtered deionized water.

PCR Amplification

A 129 basepair fragment of a putative transposon located next to the phophoserine transaminase (serC) gene of *Edwardsiella ictaluri* (GenBank: AF110153) was first amplified with conventional PCR to verify that an appropriately sized fragment was targeted. This was accomplished using two *Edwardsiella ictaluri* primers (Table 1). Each 15 $\mu$l reaction included 15 pmol of each primer; 2 nmol of each dNTP; 1×PCR buffer (10 mM Tris-HCl, pH 8.3, 50 mM KCl, 0.01% (w/v) gelatin) ABI Corporation); 1.5 mM $MgCl_2$; 1.0 U AmpliTaq Gold polymerase (ABI Corporation); and template DNA (varying amounts). In each set of reactions, 100 pg of *Edwardsiella ictaluri* DNA was used as a positive control and filtered deionized water was used as the template for the negative control. The optimized amplification profile was as follows: hotstart for 10 minutes at 94° C., followed by 40 cycles of 30 seconds at 94° C., 45 seconds at 60° C., and 1 minute at 72° C. and followed by 5 minutes at 72° C. Each reaction was run on the MJ Research PTC200 Thermalcycler. Amplification of single products of the expected size was verified by electrophoresis through 2.0% agarose gels.

All real-time PCR amplifications were performed in triplicate. Each amplification reaction mixture (25 $\mu$l) contained a DNA sample (2 $\mu$l); 1X Platinum Quantitative PCR SuperMix-UDG (Invitrogen Life Technologies, Carlsbad, Calif.) which consisted of: 0.75 U Platinum Taq DNA Polymerase, 20 mM Tris-HCl (pH 8.4), 50 mM KCl, 3 mM $MgCl_2$, 200 $\mu$M dATP, 200 $\mu$M dCTP, 400 $\mu$M dUTP, 1 U UDG; 0.2 $\mu$M of each primer (2 and 2-RevB); and 0.2 $\mu$M dual-labeled probe (Table 1). The amplification profile was as follows: 50° C. for 2 minutes, 95° C. for 2 minutes, followed by 40 cycles of 95° C. for 15 seconds and 60° C. for 1 minute. All samples were run on the iCycler™ (BioRad Laboratories). Amplification products were quantified by comparison of experimental $C_1$ (threshold cycle—defined as the PCR cycle where an increase in fluorescence first occurred) levels with those of a standard curve. The standard curve was generated from 2 replicates of serial dilutions of genomic DNA from pure *Edwardsiella ictaluri* culture. The coefficient of variation was calculated for replicates of all samples to ensure repeatability of amplification results.

Analysis of Results

The processes of DNA extraction and real-time PCR amplification required about 4.5 hours per blood sample. Amplification of the appropriately-sized PCR product was confirmed by using 1 ng of *Edwardsiella ictaluri* genomic DNA as a control template. Specificity of the primers was then tested for the 10 species of bacteria listed in Table 2. Each of the 10 species were biochemically similar to and likely to co-occur with *Edwardsiella ictaluri*. The specificity of the assay method of the present invention was demonstrated when only *Edwardsiella ictaluri* produced a PCR product. Sensitivity of the detection assay was initially determined by amplification with conventional PCR and then with real-time PCR. A set of 10-fold serial dilutions of purified *Edwardsiella ictaluri* DNA (concentrations ranging from 100 ng/nl to 10 fg/nl) was amplified yielding positive results for all concentrations of bacterial DNA (FIG. 1). Hence, the lower detection limit for the primer set was 10 fg (equivalent of 2.5 cells of *Edwardsiella ictaluri*). The cell-equivalent was calculated on data that indicates the genome size of *Edwardsiella ictaluri* to be ~3.8 fg (M. L. Lawrence, Mississippi State University, personal communication). This set of serial dilutions was used to generate a standard curve for all subsequent real-time PCR reactions as shown in FIG. 1.

Figure 2:
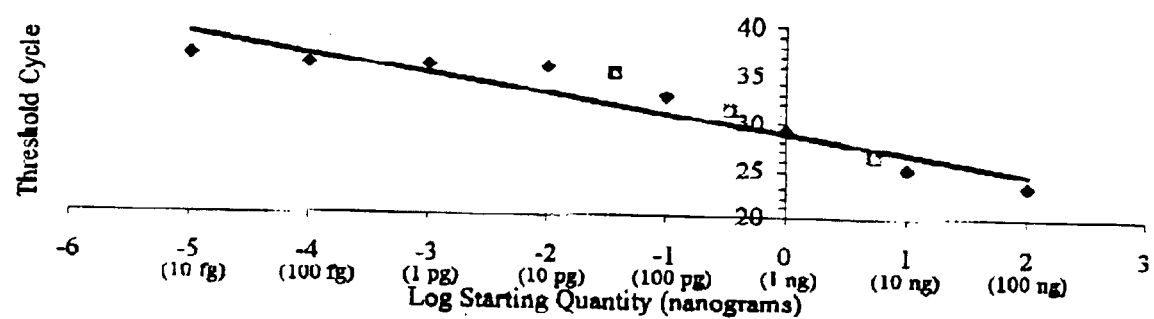
FIG. 2 is a comparison of amplification products of pure *Edwardsiella ictaluri* DNA and mixtures of whole catfish blood and pure *Edwardsiella ictaluri* DNA. Log values correspond to 1 pg, 10 pg, 100 pg, 1 ng, 10 ng, and 100 ng of bacterial DNA [♦] and 1 µL of DNA from whole catfish blood and 50 pg, 500 pg, and 5 ng of bacterial DNA [□]. Threshold cycle refers to the cycle at which fluorescence was first measured. $R^2=0.8942$, $Y=2.0402x+28.805$.
Figure 3:
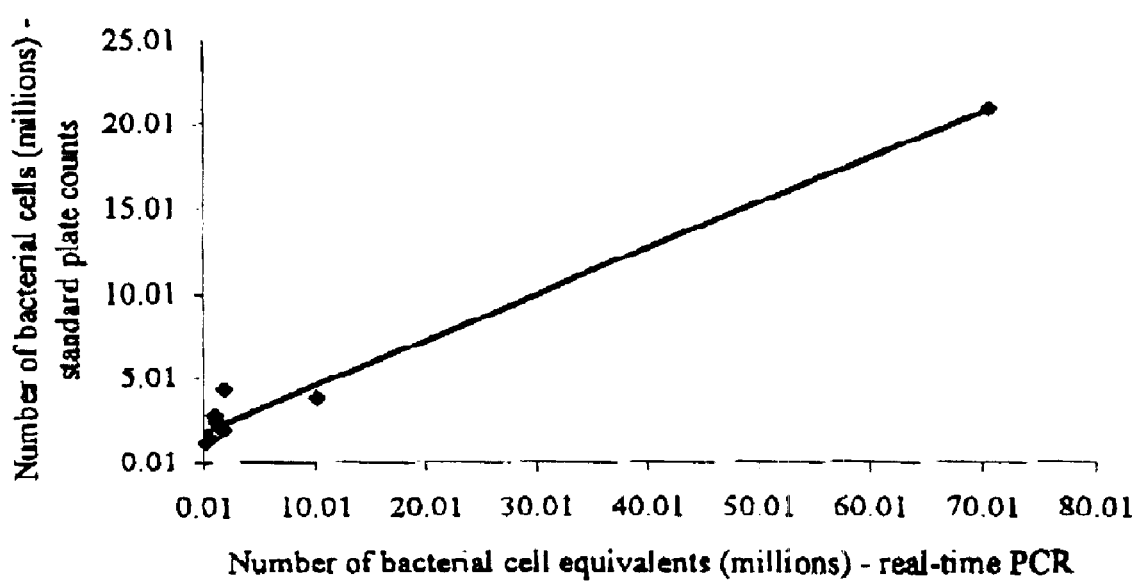
FIG. 3 is a scatterplot of real-time PCR and standard plate count data for whole blood from 9 channel catfish experimentally challenged with *Edwardsiella ictaluri*. $R^2=0.9795$, $Y=0.2701x+2\times10^6$.

DNA from clean catfish blood was mixed with serial dilutions (as above) of pure *Edwardsiella ictaluri* DNA in dual-template PCR amplification to ensure that the blood extracts did not contain any inhibiting factors for PCR amplification. No inhibition of amplification was evident as shown in FIG. 2.

Whole blood extracts from experimentally challenged fish yielded positive results in all real-time PCR amplifications, whereas control (pre-exposure) blood samples from the same fish were negative. Quantification of bacterial loads (of *Edwardsiella ictaluri*) with real-time PCR in these samples yielded results showing detection levels on the order of $10^5$ to $10^8$ cells/mL. Standard plate counts showed a similar range of bacterial loads ($10^6$ to $10^8$ cells/mL) for the same samples. The detection assay was well-correlated to plate-culture results in all cases ($R^2=0.9597$) (FIG. 1). The mean coefficient of variation for genomic PCR products was 2.11%.

CONCLUSION

Development of a sensitive, specific, and accurate detection and quantification assay for *Edwardsiella ictaluri* will improve the selective breeding program for ESC resistance. Traditional detection assays for ESC are time-consuming and have low levels of sensitivity. The real-time PCR-based assay described in the present research provides high levels of accuracy and specificity and is capable of detecting the equivalent of as few as 2.5 cells of the pathogen, *Edwardsiella ictaluri* in less than 5 hours from the time of sample collection.

The primer/probe set were specific to *Edwardsiella ictaluri* when compared to 10 biochemically similar bacterial pathogens. This indicates that the likelihood of false positives generated by contaminating species of bacteria is extremely low. This is consistent with other reports of specificity of real-time PCR assays (Nogva and Lillehaug, 1999; Nogva, et al., 2000; Vishnubhatla, et al., 2000).

The accuracy of the PCR-based detection assay was comparable to plate-culturing techniques in terms of the number of cells detected (Table 3). In all cases, the two assays yielded assessments of pathogen loads within one order of magnitude of one another. In terms of detection for acute infections, this demonstrates the utility of the real-time PCR assay.

Whole blood DNA extracts did not hinder PCR amplification of *Edwardsiella ictaluri*. Levels of amplifications from pure *Edwardsiella ictaluri* culture was highly correlated with amplification from mixtures of DNA from uninfected catfish blood and from purified genomic DNA from *Edwardsiella ictaluri*. Therefore, quantities of *Edwardsiella ictaluri* DNA derived from extracts of infected blood should be directly comparable to the standard curve generated from the DNA of pure *Edwardsiella ictaluri* culture.

Other assays that have been developed for detection of *Edwardsiella ictaluri* do not convey the advantages of the real-time PCR-based detection assay described herein because none offer the sensitivity, accuracy, and short time for processing required for early detection. These include culturing on various types of media, immunoassays, and two serological methods, fluorescent antibody technique (FAT) and enzyme linked immunosorbent assay (ELISA) (Rogers, 1981).

When applied to a selective breeding program for disease resistance, this assay can provide the tools necessary to track the early stages of infection and provide the sensitivity necessary to detect differences among fish populations/families that exhibit a variety of levels of innate disease resistance. This assay may also be used to further study the kinetics of ESC infection and to monitor clearing rates of the bacteria from natural and experimental infections.

As is true for other pathogen detection assays, real-time PCR can be readily applied to disease management of hatchery populations (Shoemaker and Klesius, 1997; Nogva and Liffehaug, 1999; Nogva, et al., 2000; Vishnubhatla, et al., 2000; Kimura, et al., 2001). Bacterial shedding and consumption of infected carcasses by healthy fish may contribute to widespread disease outbreak in a pond (Klesius, 1994). If a bacterial infection is detected before any death ensues, administration of antibiotic treatments and a timely reduction in feeding can both be viable tools in limiting an ESC outbreak. This would require regular monitoring of fish populations during spring and fall when ESC outbreaks are most likely to occur.

Real-time PCR enables rapid, specific, and accurate detection of *Edwardsiella ictaluri* that cannot be accomplished by any other currently used detection assay. This assay provides the opportunity for detailed study of disease resistance, infection kinetics, and improvement of disease management practices.

The invention of this application is described above both generically, and with regard to specific embodiments. A wide variety of alternatives known to those of ordinary skill in the art can be selected within the generic disclosure, and examples are not be interpreted as limiting, unless specially so indicated. The invention is not otherwise limited, except for the recitation of the claims set forth below. All references cited herein are incorporated in their entirety.

REFERENCES

1. Baldwin, et al., "Pathogenesis of enteric septicemia of channel catfish caused by *Edwardsiella ictaluri*: bacteriologic and light electron microscopic findings", Journal of Aquatic Animal Health, 5:189–198 (1993).
2. Bell, et al., "Detection and quantification of *Spongospora subterranea* f. sp. subterranea in soils and on tubers using specific PCR primers", European Journal of Plant Pathology, 105:905–915 (1999).
3. Francis-Floyd, et al., "Effect of water temperature on the clinical outcome of infection with *Edwardsiella ictaluri* in channel catfish", Journal of the American Veterinary Medical Association, 191:1413–1416 (1987).
4. Hawke, et al., "*Edwardsiella ictaluri* sp. nov., the causative agent of enteric septicemia of catfish", International Journal of Systematic Bacteriology, 36:396–400 (1981).
5. Kimura, et al., "Rapid, quantitative PCR monitoring of growth of *Clostridium botulinum* Type E in modified-atmosphere-packaged fish", Applied and Environmental Microbiology, 67:206–216 (2001).
6. Klesius, P.H., "Transmission of *Edwardsiella ictaluri* from infected dead to noninfected channel catfish", Journal of Aquatic Animal Health, 6:180-182 (1994).
7. Klesius, et al., "Development and evaluation of an enzyme-linked immunosorbent assay for catfish serum antibody to *Edwardsiella ictaluri*", Journal of Aquatic Animal Health, 3:94–99 (1991).
8. Leal-Klevezas, et al., "Single-step PCR for detection of *Brucella* spp. From blood and milk of infected animals", Journal of Clinical Microbiology, 33:3087–3090 (1995).
9. Leon, et al., "A PCR-based assay for the identification of the fish pathogen *Renibacterium salmoninarum*", FEMS Microbiology Letters, 115:131–136 (1994).
10. Makino, et al., "Direct detection of *Bacillus anthracis* DNA in animals by polymerase chain reaction", Journal of Clinical Microbiology, 31:547–551 (1993).
11. Miriam, et al., "PCR and Probe-PCR assays to monitor broodstock atlantic salmon (*Salmo salar* L.) ovarian fluid and kidney tissue for presence of DNA of the fish pathogen *Renibacterium salmoninarum*", Journal of Clinical Microbiology, 35:1322–1326 (1997).
12. Newton, et al., "Pathology of experimental enteric septicaemia in channel catfish, *Ictalurus punctatus* (Rafinesque), following immersion-exposure to *Edwardsiella ictaluri*", Journal of Fish Diseases, 12:335–347 (1989).
13. Nogva, et al., "Application of the 5'-nuclease PCR assay in evaluation and development of methods for quantitative detection of *Campylobacter jejuni*", Applied and Environmental Microbiology, 66:4029–4036 (2000).
14. Nogva, et al., "Detection and quantification of *Salmonella* in pure cultures using 5'-nuclease polymerase chain reaction", International Journal of Food Microbiology, 51:191–196 (1999).
15. Plumb, et al., "Survival of *Edwardsiella ictaluri* in pond water and bottom mud", The Progressive Fish-Culturist, 48:212–214 (1986).
16. Rogers, W. A., "Serological detection of two species of *Edwardsiella* infecting catfish", Developments in Biological Standards, 49:169–172 (1981).
17. Shoemaker, et al., "Protective immunity against enteric septicemia in channel catfish, *Ictalurus punctatus* (Rafinesque), following controlled exposure to *Edwardsiella ictaluri*", Journal of Fish Diseases, 20:361–368 (1997).
18. Shotts, et al., "Pathogenesis of experimental *Edwardsiella ictaluri* infections in channel catfish (*Ictalurus punctatus*), Canadian Journal of Fisheries and Aquatic Sciences, 43:36–42 (1986).
19. Vishnubhatla, et al., "Rapid 5' nuclease (TaqMan) assay for detection of virulent strains of *Yersinia enterocolitica*", Applied and Environmental Microbiology, 66:4131–4135 (2000).
20. Wise, et al., "Effect of feeding frequency and romet-medicated feed on survival, antibody response, and weight gain of fingerling channel catfish *Ictalurus punctatus* after natural exposure to *Edwardsiella ictaluri*:, Journal of the World Aquaculture Society", 29:169–175 (1998).
21. Wise, et al., "Uptake and clearance of *Edwardsiella ictaluri* in the peripheral blood of channel catfish *Ictalurus punctatus* fingerlings during immersion challenge", Journal of the World Aquaculture Society, 28:45–51 (1997).

What is claimed is:

1. A method of detecting the presence of bacteria in a tissue sample of a fish which may contain said bacteria, comprising:

obtaining a sample of tissue from a fish susceptible to infection by said bacteria;

isolating nucleic acid from said sample;

exposing said nucleic acid to a binding probe having an associated detector molecule, wherein said binding probe is SEQ ID NO.: 3; then exposing said nucleic acid to a first primer and a second primer;

amplifying said exposed nucleic acid by PCR amplification;

quantifying the PCR amplified nucleic acid by detection of said detector molecule.

2. The method of claim 1, wherein said tissue sample is blood.

3. The method of claim 1, wherein said detector molecule is a fluorescent reporter dye on one end of said probe.

4. The method of claim 3, further comprising a quencher dye on the other end of said probe.

5. The method of claim 1, wherein said bacteria is *Edwardsiella ictaluri*.

6. The method of claim 1, wherein said fish is a *Ictalurus punctatus*.

7. A method of detecting the presence of bacteria in a tissue sample of a fish which may contain said bacteria, comprising:

obtaining a sample of tissue from a fish susceptible to infection by said bacteria;

isolating nucleic acid from said sample;

exposing said nucleic acid to a binding probe having an associated detector molecule; then exposing said nucleic acid to a first primer and a second primer, wherein said first primer is SEQ NO.:1;

amplifying said exposed nucleic acid by PCR amplification;

quantifying the PCR amplified nucleic acid by detection of said detector molecule.

8. A method of detecting the presence of bacteria in a tissue sample of a fish which may contain said bacteria, comprising:

obtaining a sample of tissue from a fish susceptible to infection by said bacteria;

isolating nucleic acid from said sample;

exposing said nucleic acid to a binding probe having an associated detector molecule; then exposing said nucleic acid to a first primer and a second primer, wherein said second primer is SEQ ID NO.:2;

amplifying said exposed nucleic acid by PCR amplification;

quantifying the PCR amplified nucleic acid by detection of said detector molecule.

9. A method of detecting the presence of bacteria in a tissue sample of a fish which may contain said bacteria, comprising:

obtaining a sample of tissue from a fish susceptible to infection by said bacteria;

isolating nucleic acid from said sample;

exposing said nucleic acid to a binding probe having an associated detector molecules, wherein said binding probe is SEQ ID NO.:3; then exposing said nucleic acid to a first primer and a second primer, wherein said first primer is SEQ ID NO.:1 and said second primer is SEQ ID NO.:2;

amplifying said exposed nucleic acid by PCR amplification;

quantifying the PCR amplified nucleic acid by detection of said detector molecule.

* * * * *

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
acttatcgcc ctcgcaactc                                               20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
tgatcttctg ctgtgggctg                                               20

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
cctcacatat tgcttcagcg tcgac                                         25